United States Patent [19]
Zieve et al.

[11] Patent Number: 5,190,517
[45] Date of Patent: Mar. 2, 1993

[54] ELECTROSURGICAL AND ULTRASONIC SURGICAL SYSTEM

[75] Inventors: David A. Zieve, Lafayette; Michael S. Klicek, Boulder, both of Colo.

[73] Assignee: Valleylab Inc., Boulder, Colo.

[21] Appl. No.: 711,484

[22] Filed: Jun. 6, 1991

[51] Int. Cl.$^5$ .................. A61B 17/32; A61B 17/39
[52] U.S. Cl. ................................... 604/22; 604/35; 606/38; 606/40
[58] Field of Search ............... 604/22, 35; 606/38, 606/40

[56] References Cited

U.S. PATENT DOCUMENTS

| | | |
|---|---|---|
| 3,589,363 | 6/1971 | Banko et al. . |
| 3,693,613 | 9/1972 | Kelman . |
| 4,063,557 | 12/1977 | Wuchinich et al. . |
| 4,378,801 | 4/1983 | Oosten . |
| 4,658,819 | 4/1987 | Harris et al. ................ 606/38 X |
| 4,827,911 | 5/1989 | Broadwin et al. . |
| 4,827,927 | 5/1989 | Newton . |
| 4,903,696 | 2/1990 | Stasz et al. ................ 606/40 X |
| 4,931,047 | 6/1990 | Broadwin et al. . |
| 5,015,227 | 5/1991 | Broadwin et al. . |

*Primary Examiner*—Lee S. Cohen
*Attorney, Agent, or Firm*—Peter C. Richardson; Lawrence C. Akers; Mark Dryer

[57] ABSTRACT

An electrical circuit system which provides electrical energy to a surgical apparatus having ultrasonic fragmentation, aspiration and electrosurgical coagulation capabilities, which system also includes an impedance sensing network and automatic feedback power output control to reduce RF power output as load impedance increases, thereby reducing RF leakage current.

5 Claims, 1 Drawing Sheet

ELECTROSURGICAL AND ULTRASONIC SURGICAL SYSTEM

BACKGROUND OF THE INVENTION

The present invention relates to a system including a surgical apparatus for ultrasonically fragmenting, aspirating, and electrosurgically coagulating tissue at an operative site on a patient, and to an improvement in the electrical circuitry of such system, which improvement minimizes the RF current leakage.

The application of ultrasonically vibrating surgical devices for fragmenting and removing unwanted tissue with precision and safety has led to the development of valuable surgical procedures, and the use of ultrasonic aspirators for the fragmentation and surgical removal of tissue from a body has become well known. Initially, the technique of surgical aspiration was applied for the fragmentation and removal of cataract tissue as shown, for example, in U.S. Pat. Nos. 3,589,363 and 3,693,614; the disclosure in these patents and each of the other patents and documents mentioned herein are hereby incorporated by reference in their entirety. Later, such techniques were applied with significant success to neurosurgery and other surgical specialties where the application of ultrasonic energy through a small, hand-held device for selectively removing tissue on a layer-by-layer basis with precise control has proven feasible.

Certain devices known in the art characteristically produce continuous vibrations having a substantially constant amplitude at a frequency of about twenty to about thirty KHz up to about forty to about fifty KHz. U.S. Pat. No. 3,589,363 describes one such device which is especially adapted for use in the removal of cataracts, while U.S. Pat. No. 4,063,557 describes a device suitable for removal of soft tissue which is particularly adapted for removing highly compliant elastic tissue mixed with blood. Such devices are continuously operative when the surgeon wishes to fragment and remove tissue, and generally operate under the control of a foot switch.

One known instrument for ultrasonically fragmenting tissue at an operative site and then aspirating the tissue particles and fluid away from the site is the CUSA model System 200 ultrasonic Aspirator which is manufactured and sold by Valleylab, Inc. of Stamford, Conn.; see also U.S. Pat. No. 4,827,911. When the longitudinally oscillating metallic tip in such an aspirator is brought into contact with tissue it gently, selectively and precisely fragments and removes the tissue. Some of the advantages of this unique surgical instrument are that there is little resulting damage to healthy tissue in a tumor removal procedure, blood vessels can be skeletonized, healing of tissue is promoted, no charring or tearing of margins of surrounding tissue results, only minimal pulling of healthy tissue is experienced, and excellent tactile feedback for selectively controlled tissue fragmentation and removal is provided.

Surgeons using the CUSA ultrasonic surgical instrument have indicated a desire for additional and improved capabilities for this instrument. In particular they have requested provisions for controlled penetration of capsular membranes without damage to the organs, precise and rapid removal of fibrous tissue structures such as in mucosal proctectomy procedures, and an increased rate of tissue fragmentation and removal. During many surgical procedures wherein ultrasonic fragmentation instruments have been employed additional instruments have been required for tissue cutting and hemostasis at the surgical site. Hemostasis is needed for example in desiccation techniques for deep coagulation to dry out large volumes of tissue and also in fulguration techniques for spray coagulation to dry out the surface of tissues. See, for example, U.S. Pat. No. 4,378,801. Often an electrosurgical pencil plugged into an electrosurgical unit for tissue cutting and hemostasis and a suction probe for aspiration of fluids and tissue particles are used. Since many surgical tools are thereby required at a single surgical site, the total surgical time is increased and efficiency decreased, as the surgeon must switch among different instruments. Also, undesirable amounts of blood are lost because of the time needed to switch from a cutting or fragmenting tool to a cauterizing instrument when bleeding is observed. Additionally, by simultaneously maintaining a plurality of surgical devices at the operative site the surgeon's field of view is reduced. Furthermore, due to the complexity of the procedures, false activation of the electrosurgical pencil, when not in use, can occur, thereby causing RF burning of the patient.

Accordingly, a need has arisen for an improved surgical procedure and apparatus which remedies these problems, and meets the above-expressed desires and needs of the surgeons.

The invention described and claimed in U.S. Pat. No. 4,931,047, the entire disclosure of which is incorporated hereby by reference, remedies these problems by incorporating RF coagulating and RF cutting capabilities to the vibratable tip of an ultrasonic fragmenting and aspiration device.

Thus, U.S. Pat. No. 4,931,047 provides a surgical apparatus for performing one or more surgical procedure at a surgical site on a patient comprising: a handpiece; a tool supported by said handpiece; said tool having a vibrating tool tip; an RF current means selectively operable for providing an RF current to said tool tip for allowing performance of an electrosurgical procedure at the surgical site; a vibrating means for ultrasonically vibrating said tool tip; said tool tip having a tip opening; said tool having a tool passageway therethrough communicating with said tip opening; and an aspirating means for applying a suction pressure on said tool passageway for aspirating tissue particles and fluid at the surgical site through said tip opening through said tool passageway and away from the surgical site, said RF current means including a switching means for switching the RF current provided to said tool tip to at least an RF cutting current during ultrasonic vibration.

Surprisingly, by using the above apparatus, the fragmentation and aspiration capabilities are actually enhanced by the delivery of RF energy to the fragmentation and aspiration tip. A switching mechanism conveniently accessible to the surgeon allows him during surgery and with the instrument tip at the surgical site to instantly switch among the application of no active function, one active function, or the simultaneous application of any combination of active functions of the instrument, thereby increasing the efficacy of the instrument and decreasing the time of the surgery. The bleeding which occurs during tissue fragmentation is more quickly and better controlled. There is also provision for controllable delivery of irrigation and cooling fluids to the surgical site.

The preferred switching means for switching the RF current to the tool tip in the apparatus of U.S. Pat. No.

4,931,047 includes a metallic electrical contact in the form of a thin metal strip which makes touching contact with the electrically conducting metal connecting member attached to the tool. Although this arrangement works well when the instrument is new, since the connecting member undergoes constant vibration when the instrument is in use, a certain amount of arcing is unavoidable and this causes erosion and/or build-up of an oxide coating on the metal contact strip or the connecting member or both, and such deterioration leads to increased electrical resistance and interference with the electronic circuitry, resulting in reduced efficiency.

Subsequently, it was found that an effective non-arcing electrical contact can be made and the above effect eliminated by making the electrical contact from the switch to the acoustic connecting member through a conductive O-ring connected to the switch module through a metal contact band. Since the O-ring is located around the acoustic member and is resilient enough to expand and contract with the ultrasonic vibrations, it remains in constant contact with the member and, therefore, is not subject to arcing. Thus, in an improvement described and claimed in U.S. Pat. No. 5,015,227, the entire disclosure of which is incorporated herein by reference, the switching means for switching the RF current to the tool tip comprises a switch module for selecting the RF current, an electrically conducting metal band connected to said switch module and an electrically conductive O-ring around said connecting member and in electrical contact with said metal band.

The apparatus disclosed in U.S. Pat. Nos. 4,931,047 and 5,015,227 provides hemostasis in combination with an ultrasonically vibrating surgical fragmentation instrument and aspirator. The apparatus is an effective surgical instrument which offers both a coagulation feature and an enhanced ability to fragment and aspirate tissue in a manner which reduces trauma to surrounding tissue.

However, it was discovered that the combination of RF electrical energy from a standard electrosurgical generator with the ultrasonic surgical aspirator might allow an unacceptable level of RF leakage current to leak to the patient or the surgeon holding the instrument.

It has now been found that unacceptable high levels of leakage current are reduced or eliminated by the inclusion in the output circuit of the generator of an impedance sensing network as hereinafter described.

Although various means are known in the art for changing the level of output power of an electrosurgical generator, for example, the switching arrangement disclosed in U.S. Pat. No. 4,827,927, the present invention provides the first application of impedance sensing and automatic power output controlling at high load impedance in a system incorporating ultrasonic fragmentation, aspiration and electrosurgical coagulation capabilities.

SUMMARY OF THE INVENTION

In accordance with the invention there is provided in an electrical circuit system which provides electrical energy to a surgical apparatus for performing one or more surgical procedures at a surgical site on a patient, which apparatus comprises a handpiece, a tool supported by said handpiece, said tool having a vibrating tool tip with a tool passageway therethrough terminating in a tip opening, vibrating means for ultrasonically vibrating said tool tip and suction means for applying aspiration to aspirate tissue particles and fluid away from the surgical site and through said tip opening and tool passageway; which system comprises RF current means selectively operable for providing an RF current to said tool tip for allowing performance of an electrosurgical procedure at the surgical site; said RF current means including a generator having a pulse drive and an RF amplifier section, and switching means for switching the RF current provided to said tool tip to at least an RF coagulating current during ultrasonic vibration, the improvement wherein said system includes an impedance sensing network which provides feedback control of the output energy provided by said drive, said control automatically acting to reduce the RF output energy as load impedance increases, whereby RF leakage current is restrained to a safe low level.

Since many of the terms and expressions used herein are terms of art which are not always applied in the same manner, the following definitions are given for clarification:

As used herein the term electrosurgical generator means a unit for generating radio frequency (RF) electrical energy which is transmitted through an insulated line to an electrosurgical instrument comprising a handpiece which supports an active electrode. The active electrode delivers the electrical energy to a patient at the site of the operation and the electrical circuit back to the generator is completed through the body of the patient and via a return electrode placed on the patient's body at a position remote from the operation site.

An isolated generator is an electrosurgical generator whose return terminal is not connected to ground for RF energy. Generally, an isolated generator is preferred for electrosurgical operations.

The active electrode used for cutting generally has the shape of a small flat blade, usually made from a metal such as stainless steel. Electrodes used for fulguration (or coagulation) may have other shapes.

Electrosurgical cutting occurs when intense sparks pass between the active blade electrode and the tissue contacted. As the temperature rises rapidly in the contacted cells, the water inside the cell boils and the cell explodes. This causes a cavity to form and allows the blade to travel quickly to the next group of cells. The tissue impedances encountered in cutting during open procedures range from about 1000 to 4000 ohms.

Electrosurgical desiccation occurs when a large active electrode to tissue contact area and a relatively high current causes tissue to dry out and sometimes even char. This effect prevents the tissue from bleeding. Electrosurgical desiccation is a form of electrosurgical coagulation.

Electrosurgical fulguration occurs when a spark jumps from the active electrode to the tissue through a wide air gap (approximately 1.5 to 3 mm). The electrosurgical output voltage must be high to enable the spark to jump the air gap. The tissue effect is similar to desiccation, but a wider area is covered. Electrosurgical fulguration, like desiccation, is also referred to as electrosurgical coagulation.

An electrosurgical waveform is a display, as seen on an oscilloscope, of the RF voltage transmitted to the patient. Generally, the frequency is within the range of about 500 to 1000 KHz.

Crest factor is the ratio of the peak voltage to the root mean square (RMS) voltage of a periodic waveform. In electrosurgery, generally an output with a high waveform crest factor is better for fulgurating tissue.

High impedance tissue is generally adipose, or fatty tissue. Cartilage, connective tissue and certain organs are also high impedance tissues. Muscle is a low impedance tissue. High impedance refers to the ability of the tissue to conduct RF energy. Low impedance tissues are better conductors, R.F. leakage current is current that bypasses the return electrode. The return electrode is placed on the patient's thigh or underside. This leakage current is dangerous and can cause the patient to be burned if it is excessive.

In view of the hazard of excessive RF leakage current, equipment used in electrosurgical operations must comply with certain standards, for example, the standard prescribed by International Electrical Commission (IEC) 601-2-2 which states that the RF leakage current through a non-inductive 200 ohm resistor to ground shall not exceed 150 ma. In the electrical circuit system of the present invention the RF leakage current is always well below 150 ma and the equipment satisfies the IEC 601-2-2 standard.

BRIEF DESCRIPTION OF THE DRAWINGS

The invention will be more particularly described with reference to a preferred embodiment as illustrated in the accompanying drawings, in which.

DETAILED DESCRIPTION OF THE INVENTION

Figure 1:
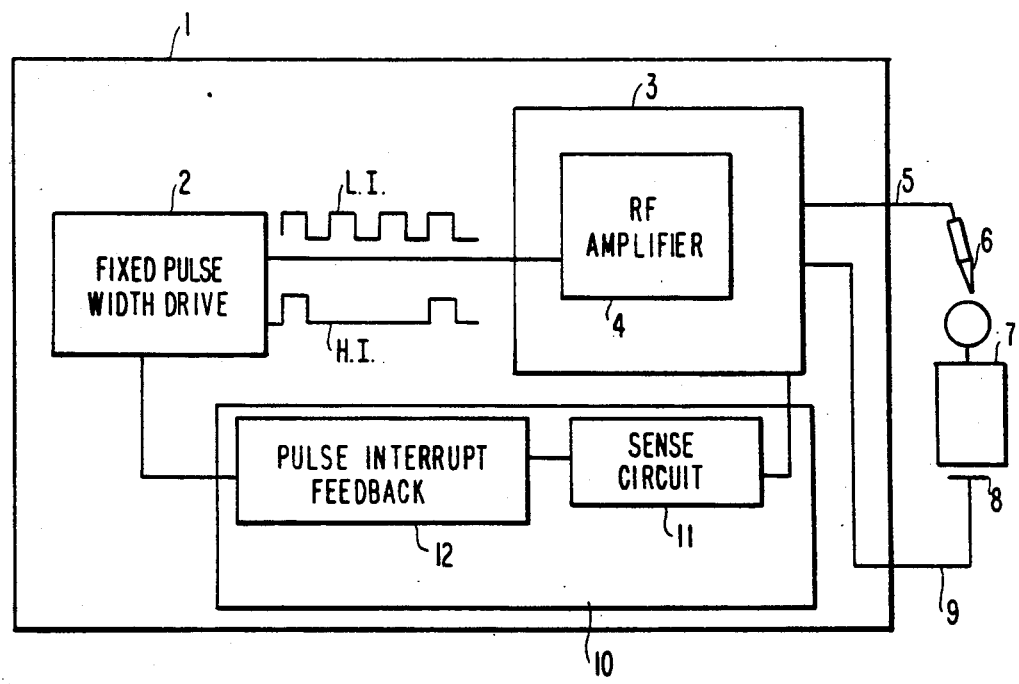
FIG. 1 is a schematic block diagram of part of a system incorporating an impedance sensing network according to the invention.
Figure 2:
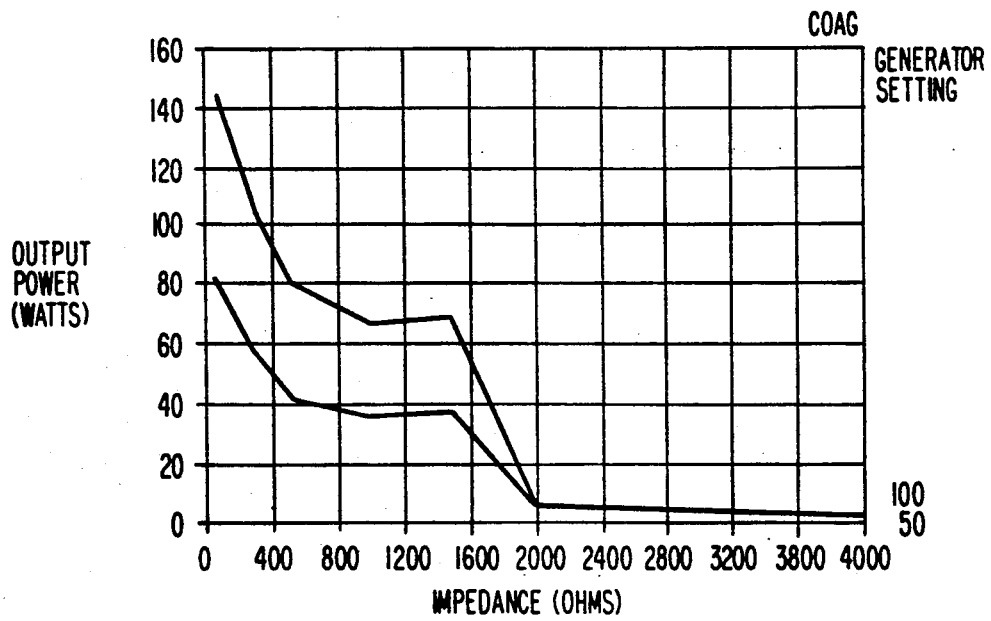
FIG. 2 is a graph showing the controlled power output reduction with increasing load impedance.

The system part illustrated in FIG. 1 of the drawings is a schematic representation of a printed circuit board assembly 1 in the output stage of a standard electrosurgical generator, for example, a Force 2 Electrosurgical Generator manufactured by Valleylab, Inc., Boulder, Colo. The RF power supply includes a fixed pulse width drive 2 which, at low impedance load, provides RF current having a voltage waveform having a pulse width of 0.85 $\mu$ sec. represented by L.I. (not to scale). The fixed pulse width drive is gated at a 32 $\mu$ sec. repetition rate for low tissue impedance of about 50 to 1500 ohm. The RF current from the drive passes to an amplifier section 3, comprising a class C RF amplifier 4. Several power FET devices provide 100 watts RF power at 300 ohm load impedance. The RF output is transformer coupled through line 5 to the active electrode 6. The primary voltage of the transformer is used to sense tissue impedance. When the unit is in operation, the circuit back to the generator is completed through the patient 7, return electrode 8 and line 9. A tissue impedance sensing network 10 is connected to the primary winding of the RF output transformer in section 3. This network comprises a sense circuit 11 and a pulse interrupt feedback 12. When the ultrasonic accessory is activated the tissue impedance data from the amplifier section is processed and used to trigger the interrupt signal to the pulse width drive. When the patient impedance is high, i.e. above about 1500 ohm, the RF power output is interrupted to increase the repetition rate period to greater than 100 sec., giving a waveform represented by H.I. In addition, the primary load impedance on the RF output transformer is decreased to reduce RF leakage current.

The electrosurgical coagulating waveform provided by the system according to the invention has the following characteristics at the maximum setting of 100 watts:

(1) It provides approximately 100 watts of output power at the rated load impedance of 300 ohms. In addition, at least 70 watts of output power is available in the impedance range of 30 to 1200 ohms.

(2) It provides less than 20 watts of output power above 1800 ohms load impedance.

(3) It provides approximately 2500 V peak to peak (p-p) under no load.

(4) It provides a waveform with a crest factor less than 4.0 at from about 100 to 1500 ohms load impedance.

(5) It provides a waveform with a crest factor greater than 7.0 at from about 1800 to 5000 ohms load impedance.

Because the waveform provided by the invention has enough p-p output voltage to fulgurate, a spark (longer than 1.5 mm) will appear when the active electrode is applied near bleeding vascular tissue. Alternatively, if the electrode is left in contact with the tissue, enough power output is available to desiccate the bleeding vessels. This waveform is unique because it supplies enough power to desiccate large vessels while maintaining extremely low RF leakage; and it allows fulguration (a long spark) while maintaining extremely low RF leakage.

We claim:

1. In an electrical circuit system which provides electrical energy to a surgical apparatus for performing one or more surgical procedures at a surgical site on a patient, which apparatus comprises a handpiece, a tool supported by said handpiece, said tool having a vibrating tool tip with a tool passageway therethrough terminating in a tip opening, vibrating means for ultrasonically vibrating said tool tip and suction means for applying aspiration to aspirate tissue particles and fluid away from the surgical site and through said tip opening and tool passageway; which system comprises RF current means selectively operable for providing an RF current to said tool tip for allowing performance of an electrosurgical procedure at the surgical site; said RF current means including a generator having a pulse drive and RF amplifier section, and switching means for switching the RF current provided to said tool tip to at least an RF coagulating current during ultrasonic vibration, the improvement wherein said system includes means for providing feedback control of the output energy provided by said drive comprising an impedance sensing network which automatically acts to reduce the RF output energy as load impedance increases, whereby RF leakage current is restrained to a safe low level.

2. A system according to claim 1, in which the generator is an electrosurgical generator wherein the drive provides about 100 watts of output RF power at a rated load impedance of 300 ohms, at least 70 watts of output RF power at a load impedance in the range of about 30 to 1200 ohms and less than 20 watts of output RF power at a load impedance above about 1800 ohms.

3. A system according to claim 1, in which the pulse drive provides a waveform with a crest factor less than 4.0 at a load impedance of from about 100 to 1500 ohms.

4. A system according to claim 1, in which the pulse drive provides a waveform with a crest factor greater than 7.0 at a load impedance of from about 1800 to 5000 ohms.

5. A system according to claim 1, in which the RF leakage current during surgical operations is less than 150 mA when measured according to IEC Standard 601-2-2 for isolated electrosurgical devices.

* * * * *